United States Patent [19]

Yukinaga et al.

[11] 4,061,490
[45] Dec. 6, 1977

[54] POST-HARVEST PLANT PRESERVING COMPOSITIONS

[75] Inventors: Hisajiro Yukinaga, Kusatsu; Hideo Kano, Ibaraki; Masaru Ogata, Kobe, all of Japan

[73] Assignee: Shionogi & Co., Ltd., Osaka, Japan

[21] Appl. No.: 635,449

[22] Filed: Nov. 26, 1975

Related U.S. Application Data

[63] Continuation-in-part of Ser. No. 432,889, Jan. 14, 1974, abandoned.

[30] Foreign Application Priority Data

Jan. 18, 1973  Japan .................................. 48-8065

[51] Int. Cl.$^2$ .............................................. A01N 3/02

[52] U.S. Cl. ............................................ 71/68; 71/92; 71/113; 424/132; 424/249; 424/308

[58] Field of Search ............... 424/330, 132, 308, 249; 71/68, 92, 113

[56] References Cited

PUBLICATIONS

Chemical Abstracts, vol. 77 (1972), p. 151988u.
Chemical Abstracts, vol. 77 (1972), p. 164313v.
Merck Index, 7th Ed. 1960, pp. 631–632, 665,991.

Primary Examiner—V. D. Turner
Attorney, Agent, or Firm—Wenderoth, Lind & Ponack

[57] ABSTRACT

Post-harvest plant preserving compositions which comprise a naphthoquinone derivative as an active ingredient.

11 Claims, No Drawings

POST-HARVEST PLANT PRESERVING COMPOSITIONS

This application is a continuation-in-part of Ser. No. 432,889, filed Jan. 14, 1974, now abandoned.

This invention relates to post-harvest plant preserving compositions and methods for preservation. More particularly, this invention is concerned with compositions for preservation of post-harvest plants containing a naphthoquinone derivative.

The naphthoquinone derivative contained in the said composition is 2-benzimidoyl-3-hydroxy-1,4-naphthoquinone represented by the following formula [I]:

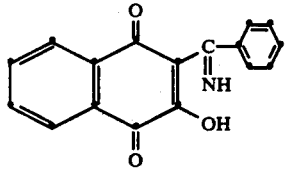

The compound of the formula [I] has been found to significantly preserve freshness of plants, especially against biological deterioration resulting from factors other than bacteria or fungi. Accordingly, a basic object of this invention is to provide compositions for preservation of post-harvest plants containing an effective amount of 2-benzimidoyl-3-hydroxy-1,4-naphthoquinone in combination with suitable agricultural carriers and other ingredients. A further object of the invention is to provide a method of preserving post-harvest plants against biological deterioration resulting from factors other than bacteria or fungi by application of the said compositions. These and other objects and the manner in which they are accomplished will become apparent to those conversant with the art from the following descriptions.

The naphthoquinone derivative [I] contained in the composition of the invention can be prepared by the method described in British Pat. No. 1,336,973 and "Chemical Abstracts" vol. 77, 151988u (1972). Both disclosures refer to antibacterial, anti-fungal activities as well as plant-growth regulating activity of the compound of this invention and its analogous compounds. However, the compound of this invention shows neither anti-bacterial for anti-fungal activity.

The mechanism of plant wilt disease has not been clearly elucidated, but it is assumed that post-harvest plants lose freshness by attack of bacteria and fungi as well as biological deterioration resulting from factors other than bacteria or fungi, more specifically senescence. Most preservatives for cut flowers on the market consist of bacteriocide and fungicide. However, the aim of this invention provides compositions to keep the freshness of post-harvest plants against biological deterioration resulting from factors other than bacteria or fungi, more specifically by retarding senescense. In other words, the composition of this invention preserves post-harvest plants by a hormonal mechanism.

The compound [I] has been found to show plant-growth regulating activity as described above. However, it is generally recognized in this field that plant-growth regulating activity is clearly not related to retarding senesence activity. The present invention is based on a discovery that the known compound with plant-growth regulating activity posesses senescense-retarding activity. More precisely, it is based on the discovery that the naphthoquinone derivative [I] effectively inhibits petal-developing, deterioration, color-fading, wilting and loss of edibility in post-harvest plants by a hormonal mechanism.

The post-harvest plants in the present invention include cut plants. Examples of cut plants are cut flowers for decoration and ornament (e.g. rose, snapdragon, poppy, carnation, chrysanthemum, tulip, iris, daffodil, Chinese bellflower, peony), cut green leaf plants, cut trees (e.g cherry, plum, azalea, maple, magnolia, camellia, hydrangea) and leaf vegetables (e.g. parsely) and the like.

The compositions of the present invention can be used to preserve the post-harvest plants at any stage of transportation, storage and application for ornament and decoration.

The effect of the composition can be recognized preferably for any of the above cut plants and most preferably for cut flowers.

To illustrate the effect of preserving post-harvest plants with the compound [I], test results with cut flowers are shown together with results with some known agents or compositions in the following tables.

The tables show that the preserving effect of the compound [I] is superior to the known agents or compositions. Further, it is shown that the effect of the compound [I] is enhanced by the addition of antiseptic and nutrient and affected probably synergetically by adding plant growth regulant.

Table 1

| Treatment | ppm | Preserving effects on cut rose flower "Superstar" by continuous treatment | | | | | | | |
|---|---|---|---|---|---|---|---|---|---|
| | | Days after Treatment | | | | | | | |
| | | 0 | 1 | 2 | 3 | 4 | 5 | 6 | 7 |
| 2-Benzimidoyl- | 5 | 1.7 | 3.7 | 4.3 | 4.3 | 5.3 | 5.7 | 6.0XX | 6.0XX |
| 3-hydroxy-1,4- | 2.5 | 1.3 | 3.7 | 4.7 | 5.0 | 6.0 | 6.0 | 6.0X | 6.5X |
| naphthoquinone | 1 | 1.7 | 3.3 | 4.0 | 4.0 | 5.0 | 5.0 | 6.0X | 6.0X |
| $N^6$-Benzylamino-purime* | 10 | 1.7 | 4.0 | 6.0 | 7.0[a] | 8.0 | 9.0 | 10.0 | 10.0X |
| Cornell Solution* | | 1.7 | 3.7 | 6.3 | 8.0 | 9.3[b] | 10.0 | 10.0XX | 10.0XX |
| Washington Solution* | | 1.7 | 3.3 | 4.7 | 6.7 | 7.7[c] | XXX | XXX | XXX |
| Untreated | | 1.7 | 3.7 | 5.0 | 7.7 | 8.7 | 9.5X | 9.0XX | 9.0XX |

[a]Blacking around the leaf edge
[b]Yellowing of the leaf
[c]Falling of the leaf
*Known agents

Test Method

Cut rose buds "Superstar" were put in test solutions containing 2-benzimidoyl-3-hydroxy-1,4-naphthoquinone at the concentration of 5, 2.5 or 1 parts per million (ppm). Each group consisting of 3 roses was kept at room temperature and observed.

Figures in the table show degree of petal development (average of 3 individuals) graded with 0 for bud and 10 for full bloom. X indicates number of the flowers of which petals fell or withered.

Cornell solution consists of 8-hydroxyquinoline (200 ppm), silver acetate (500 ppm) and sucrose (5%). Washington solution consists of 8-hydroxyquinoline (300 ppm), succinic acid 2,2-dimethylhydrazide (500 ppm) and sucrose (3%).

lets or the like in compliance with the form of application intended. The composition may normally contain from about 0.00001 percent by weight to about 90 percent by weight of 2-benzimidoyl-3-hydroxy-1,4-naphthoquinone as an active ingredient, the amount depending on the form of composition as well as the use intended. To formulate the composition, suitable gaseous, liquid, or solid carriers and other ingredients including surface active agents are used in addition to the naph- Table 2.

| Treatment | ppm | Preserving effects on cut rose flower "Superstar" by temporary treatment Days after Treatment | | | | | | | |
|---|---|---|---|---|---|---|---|---|---|
| | | 0 | 1 | 2 | 3 | 4 | 5 | 6 | 7 |
| 2-Benzimidoyl-3-hydroxy-1,4-naphthoquinone (One hour treatment) | 100 | 2.0 | 3.7 | 4.0 | 4.3 | 5.0 | 5.5X | 6.0XX | 6.0XX |
| | 10 | 1.7 | 4.0 | 4.7 | 5.3 | 6.3 | 7.0 | 8.0X | 8.0X |
| | 1 | 1.7 | 4.0 | 5.7 | 7.3 | 8.0 | 8.3 | 9.3 | 9.3 |
| 2-Benzimidoyl-3-hydroxy-1,4-naphthoquinone (Fifteen hours treatment) | 100 | 1.3 | 3.3 | 4.0 | 4.0 | 4.3 | 4.3 | 5.3 | 5.3 |
| | 10 | 1.3 | 3.0 | 4.0 | 4.0 | 4.0 | 4.0 | 5.0 | 5.0X |
| | 1 | 1.7 | 3.3 | 4.7 | 6.7 | 7.7 | 7.0X | 7.5X | 8.0X |
| $N^6$-Benzylaminopurine* | 10 | 1.7 | 4.0 | 6.0 | 7.0$^a$ | 8.0 | 9.0 | 10.0 | 10.0X |
| Cornell Solution* | | 1.7 | 3.7 | 6.3 | 8.0 | 9.3$^b$ | 10.0 | 10.0XX | 10.0XX |
| Washington Solution* | | 1.7 | 3.3 | 4.7 | 6.7 | 7.7$^c$ | XXX | XXX | XXX |
| Untreated | | 1.7 | 3.7 | 5.0 | 7.7 | 8.7 | 9.5X | 9.0XX | 9.0XX |

$^a$:Blacking around the leaf edge
$^b$:Yellowing of the leaf
$^c$:Falling of the leaf
*Known agents

Test Method

Cut rose buds "Superstar" were kept in test solution containing 2-benzimidoyl-3-hydroxy-1,4-naphthoquinone at the concentration of 100, 10 or 1 ppm for 1 or 15 hours and then put in plain water and observed in the same manner as in Table 1.

thoquinone derivative [I], and conventional techniques for dissolving, mixing, blending, crushing, granulating, or tabletting may optionally be adopted.

The surface active agents used in preparing the compositions of the present invention can be wetting, dispersing, or emulsifying agents. They may act, for example, as wetting agents for wettable powders and dusts, Table 3

| Treatment | Preserving effect of compositions on cut rose flower "Superstar" | | | | | | | |
|---|---|---|---|---|---|---|---|---|
| | Days after Treatment | | | | | | | |
| | 0 | 1 | 2 | 3 | 4 | 5 | 6 | 7 |
| Solution 1 | 1.3 | 2.3 | 2.7 | 3.3 | 4.3 | 4.3 | 4.3 | 4.3 |
| Solution 2 | 1.3 | 2.3 | 2.7 | 3.3 | 4.3 | 5.0 | 5.0 | 5.0 |
| Solution 3 | 1.3 | 1.7 | 2.7 | 4.0 | 4.7 | 4.7 | 5.0XX | 5.0XX |
| 8-Hydroxyquinoline* 200 ppm | 1.0 | 2.0 | 3.0 | 5.0 | XXX | XXX | XXX | XXX |
| Untreated | 1.3 | 2.0 | 3.0 | 5.0 | 6.3 | 7.7 | 7.5X | 8.0XX |

*Known agent

Test Method

Cut rose buds "Superstar" were kept in test solution 1, 2 and 3 composed of the following ingredients, respectively, for 15 hours then put in plain water, and observed in the same manner as in the Table 1.

Solution 1 : 2-benzimidoyl-3-hydroxy-1,4-naphthoquinone 100 ppm, silver acetate 50 ppm Solution 2 : 2-benzimidoyl-3-hydroxy-1,4-naphthoquinone 100 ppm, silver acetate 50 ppm, sucrose 5%

Solution 3 : 2-benzimidoyl-3-hydroxy-1,4-naphthoquinone 100 ppm, succinic acid 2,2-dimethylhydrazide 500 ppm It is apparent from the tables that the test compound has a marked preserving effect on cut flowers. In addition, the preservative effect has been found on other post-harvest plants.

The compositions of the present invention may be prepared in various conventional forms such as aerosols, emulsions, solutions, emulsifiable concentrates, wettable powders, pastes, dusts, granules, pellets, tabas dispersing agents for wettable powders and suspensions, and as emulsifying agents for emulsions and emulsifiable concentrates. Surfactants may also enhance the biological activity of the active ingredient.

Suitable surface active agents for use in the composition include polyethylene glycol esters with fatty acids; polyethylene glycol ethers with alkylphenols or with long-chain aliphatic alcohols; polyethylene glycol ethers with sorbitan fatty acid esters; and polyoxyethylenethio ethers. Other suitable surfactants include ammonium, alkali, or alkaline earth salts of alkylaryl sulfonic acids; ammonium, alkali, or alkaline earth fatty alcohol sulfates; fatty acid esters of ammonium, alkali or alkaline earth isothionates or taurates; ammonium, alkali or alkaline earth salts of lignin sulfonic acids; methylated or hydroxyethylated cellulose; polyvinyl alcohols; alkyl-substituted polyvinyl pyrrolidones; ammonium, alkali, or alkaline earth salts of polymerized alkylnaphthalene sulfonic acids; and long-chain quaternary ammonium compounds.

Examples of gaseous carriers include butane, nitrogen, carbon dioxide, freon (Trade Mark), and other inert gases. Liquid carriers for the present composition may be water, or suitable inert organic solvents such as aliphatic hydrocarbons (e.g. pentane, hexane, cyclohexane, petroleum ether, gasoline, kerosene), aromatic hydrocarbons (e.g. benzene, toluene, xylene), halogenated hydrocarbons (e.g. methylene chloride, chloroform, carbon tetrachloride, trichloroethane), ketones (e.g. acetone, methyl ethyl ketone), ethers (e.g. ether, isopropyl ether, tetrahydrofuran, dioxane), esters (e.g. ethyl acetate, amyl acetate) or alcohols (e.g. methanol, ethanol, butanol). Solid carriers may be, for example, mineral powders (e.g. clay, talc, kaoline, bentonite, diatomaceous earth, silica gel), vegetable powders (e.g. soybean powder, wheat powder), or other powders conventionally used as agricultural solid carriers or diluents.

The composition may be diluted before application to a concentration appropriate for the purpose intended, usually from about $10^{-6}$ to $10^{-2}$ % by weight. Accordingly, the amount of the naphthoquinone derivative [I] is from about $10^{-2}$ to $10^2$ μg/g when the composition is applied to plants.

The composition with or without dilution can be applied to plants by various methods depending on the purpose intended, such as spraying a solution directly onto green leafy plants, ornamental flowers or leaf vegetables, putting cut flowers continuously or temporarily in a solution prepared by dissolving tablets or granules in water, plastering an ointemnt onto the cut end of plants, and the like.

If desired, the composition of the present invention may contain, in addition to the naphthoquinone derivative [I], antiseptics (e.g. silver acetate, benzoic acid ester, methenamine, methenamine anhydromethylenecitrate), nutrients (e.g. sucrose, gluclose, lactose, fructose) or plant growth regulants (e.g. succinic acid 2,2-dimethylhydrazide, maleinic hydrazide), and the like.

The following examples are given solely for the purpose of illustration and are not to be construed as limiting the invention.

EXAMPLE 1

An emulsifiable concentrate of the following composition is prepared:

| | | |
|---|---|---|
| 2-Benzimidoyl-3-hydroxy-1,4-naphthoquinone | 0.1 | % by weight |
| Silver acetate | 5.0 | % by weight |
| Polyethylene alkylaryl ether | 10.0 | % by weight |
| Acetone | 84.9 | % by weightf |

The emulsifiable concentrate is diluted 10— to 100—fold with water before application.

EXAMPLE 2

An emulsifiable concentrate of the following composition is prepared:

| | | |
|---|---|---|
| 2-Benzimidoyl-3-hydroxy-1,4-naphthoquinone | 0.001 | % by weight |
| Silver acetate | 0.05 | % by weight |
| Sucrose | 5.0 | % by weight |
| Polyethylene alkylaryl ether | 5.0 | % by weight |
| Acetone | 60.0 | % by weight |
| Benzene | 30.0 | % by weight |

EXAMPLE 3

An emulsifiable concentrate of the following composition is prepared:

| | | |
|---|---|---|
| 2-Benzimidoyl-3-hydroxy-1,4-naphthoquinone | 0.0001 | % by weight |
| Succinic acid 2,2-dimethylhydrazide | 0.05 | % by weight |
| Lactose | 1.0 | % by weight |
| Water | 99.0 | % by weight |

EXAMPLE 4

A mixture of the following composition is prepared:

| | |
|---|---|
| 2-Benzimidoyl-3-hydroxy-1,4-naphthoquinone | 1 % by weight |
| Bentonite powder | 99 % by weight |

After blending, the mixture is kneaded with water, granulated, and dried to obtain granules. Before application, 0.5 g to 1 g of the granules is dissolved in 10 l of water.

EXAMPLE 5

An emulsifiable concentrate of the following composition is prepared:

| | |
|---|---|
| 2-Benzimidoyl-3-hydroxy-1,4-naphthoquinone | 1 % by weight |
| Butyl benzoate | 0.5 % by weight |
| Water | 98.5 % by weight |

The emulsifiable concentrate is diluted 100— to 200—fold with water before application.

EXAMPLE 6

A dust of the following composition is prepared:

| | |
|---|---|
| 2-Benzimidoyl-3-hydroxy-1,4-naphthoquinone | 30 % by weight |
| A mixture of talc and kaoline | 70 % by weight |

The mixture is blended and ground to obtain a dust.

What is claimed is:

1. A composition for preserving post-harvest plants which comprises, as active ingredient, from about 0.00001 to about 90 percent by weight of 2-benzimidoyl-3-hydroxy-1,4-naphthoquinone, and an agriculturally acceptable carrier therefor.

2. The composition of claim 1 in the form of an aerosol, solution, emulsion, emulsifiable concentrate, wettable powder, paste, dust, granule, pellet or tablet.

3. The composition of claim 1, further comprising a surface active agent.

4. The composition of claim 1, further comprising a nutrient selected from the group consisting of sucrose, glucose, fructose and lactose.

5. The composition of claim 1 further comprising an antiseptic selected from the group consisting of silver acetate, butyl benzoate, methenamine and methenamine anhydromethylenecitrate.

6. The composition of claim 1 further comprising a plant growth regulant selected from the group consisting of succinic acid 2,2-dimethylhydrazide and maleinic hydrazide.

7. The composition of claim 1, wherein the post-harvest plants are cut flowers.

8. A method of preserving post-harvest plants which comprises applying to the post-harvest plants an effective amount of the composition claimed in claim 1.

9. The method according to claim 9, wherein the post-harvest plants are cut flowers.

10. A method of retarding senescence in cut flowers which comprises applying to the cut flowers an effective amount of a composition comprising, as active ingredient, from about 0.00001 to about 90 percent by weight of 2-benzimidoyl-3-hydroxy-1,4-naphthoquinone, and an agriculturally acceptable carrier therefor.

11. The method according to claim 10, wherein the senescence is petal developing.

* * * * *